United States Patent [19]

Camp et al.

[11] Patent Number: 4,677,304
[45] Date of Patent: Jun. 30, 1987

[54] APPARATUS FOR DETERMINING THE STABILITY OF FOAM

[75] Inventors: Mark A Camp, Hanworth; Frank T. Lawrence, Ashford Common, both of England

[73] Assignee: The British Petroleum Company p.l.c., London, England

[21] Appl. No.: 729,115

[22] Filed: Apr. 30, 1985

[30] Foreign Application Priority Data

May 5, 1984 [GB] United Kingdom ............... 8411608

[51] Int. Cl.$^4$ ............................................ G01N 21/00
[52] U.S. Cl. .................................. 250/577; 73/60.1; 356/436
[58] Field of Search ............... 73/60.1, 64; 250/564, 250/573, 577; 356/7, 372, 436

[56] References Cited

U.S. PATENT DOCUMENTS

| | | | |
|---|---|---|---|
| 3,454,759 | 7/1969 | Calhoun | 356/436 X |
| 3,915,570 | 10/1975 | Skala | 356/73 |
| 4,061,016 | 12/1977 | Noel et al. | 250/577 |
| 4,084,426 | 4/1978 | Gales | 73/60.1 |

FOREIGN PATENT DOCUMENTS 2551260 9/1975 Fed. Rep. of Germany .
2551260 5/1977 Fed. Rep. of Germany ....... 73/60.1
3022848 1/1982 Fed. Rep. of Germany ....... 73/60.1

OTHER PUBLICATIONS

J. Phys. Chem. 59 pp. 863–866 (1955), Ross, S. et al., "The Transmission of Light by Stahle Foams".
Ross, S. et al., "The Transmission of Light by Stable Foams".

Primary Examiner—Eugene R. LaRoche
Assistant Examiner—David Mis
Attorney, Agent, or Firm—Morgan & Finnegan

[57] ABSTRACT

Apparatus for determining the stability of a foam comprising a light source (1), a foam sample cell (2), a light sensitive cell (3) having a linear output voltage- or current-exposed area relationship, a voltmeter or ammeter (9) connected to the light sensitive cell (3) and a device (11) responsive to the output from the voltmeter for integrating a voltage-time curve or a current-time curve directly and dividing this area by the difference in voltage or current between that observed in the absence of foam and that observed immediately after foam has been formed to give the average foam lifetime. The light source (1), the foam sample cell (2) and the light sensitive cell (3) are positioned in line and are enclosed in a light-tight box (4).

8 Claims, 3 Drawing Figures

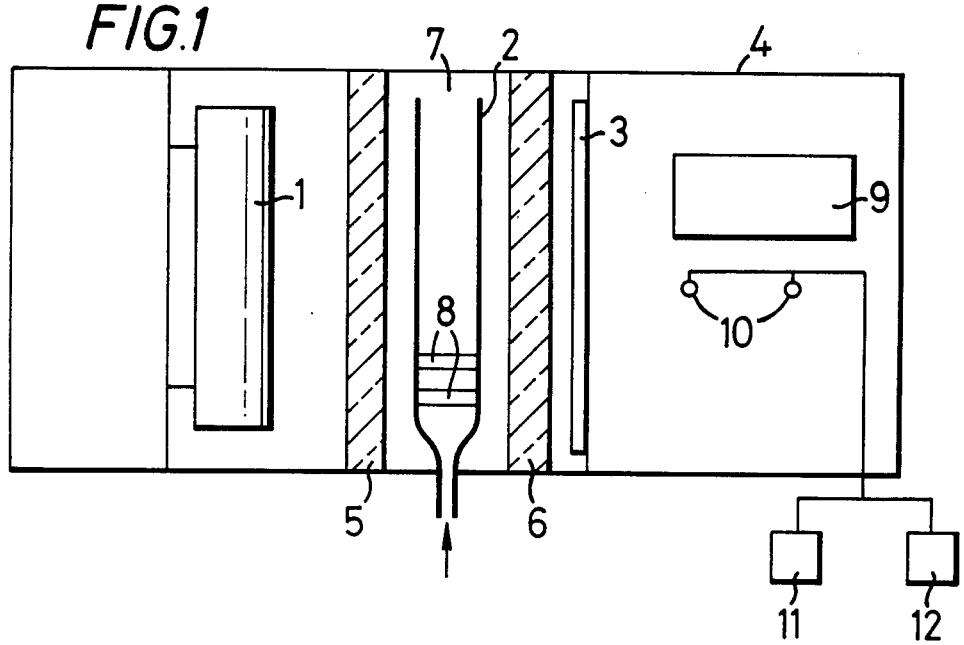
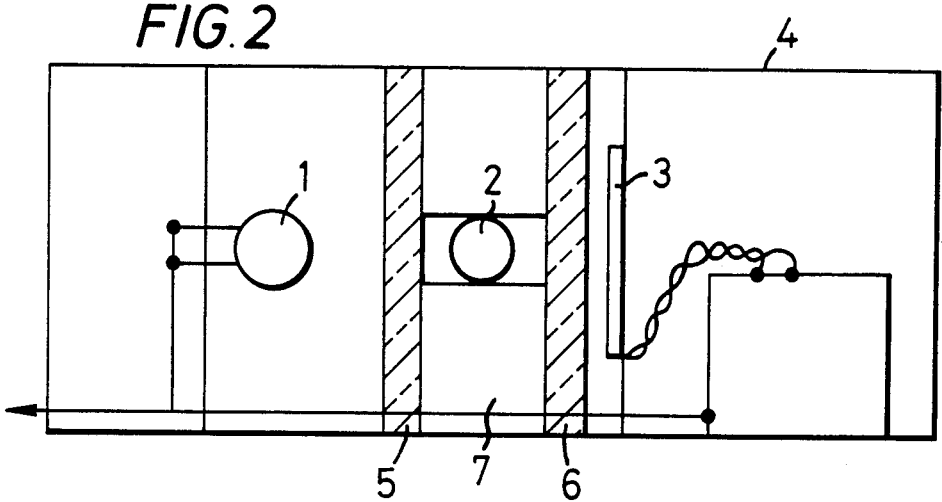

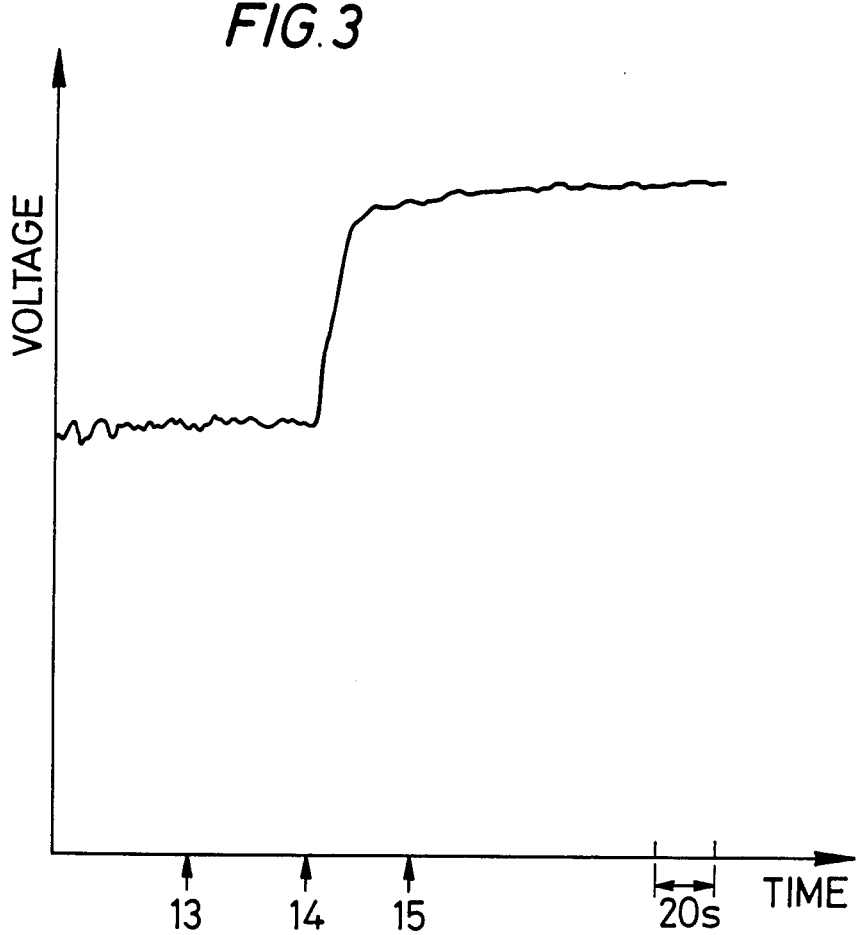

APPARATUS FOR DETERMINING THE STABILITY OF FOAM

This invention relates to a cell for determining the stability of a foam.

Foams occur in many situations and may be beneficial, such as those used in fire fighting and froth flotation, or harmful such as those occurring in gas oil separators and distillation columns.

When oil is produced from a well, it is forced by pressure from the reservoir up the well to the surface. As the oil rises, the pressure becomes less and gas associated with the oil is progressively released from solution.

After emerging from the well, it is usually necessary to treat the mixture of liquid oil and gas to remove free gas and dissolved gas which may come out of solution when the oil is maintained near atmospheric pressure, for example, during transport in a tanker.

Separation may be carried out near the wellhead or at a distant location after the oil and gas have been pumped under high pressure through a pipeline.

Separation is effected in a vessel known as a separator. Various types of separator are known. One common type is the horizontal separator which comprises a horizontal cylinder containing a system of baffles, defoamers and mist extractors. The crude enters at one end and flows towards an outlet at the other end. During the time it takes to do this, the gas bubbles out of solution and leaves the separator by a gas outlet at the top.

Sometimes the crude oil and gas form a stable foam in separators, particularly under high throughput conditions, with the result that liquid oil carries over in the gas stream.

Stable foams are of two types, known as stabilised and live foams respectively. A stabilised foam is one created by the passage of gas through a liquid. A live foam is created by gas dissolved within a liquid escaping when the liquid is subjected to a sudden pressure drop.

The stability of a foam depends on two main factors: the tendency of the liquid to drain from the foam and the resistance of the foam bubbles to rupture.

In certain instance it is advantageous to inject an anti-foam additive, e.g., a silicone, into the oil stream before it enters the separator. This additive destabilises the foam and in effect increases the handling capacity of the separator.

Additives, of course, vary in their activity, depending to some extent on their intrinsic properties and to some extent on the environment in which they operate, for example the composition of the crude oil.

We have now devised equipment which is suitable for use in determining the stability of foam and hence the efficiency of anti-foam agents.

According to the present invention there is provided apparatus for determining the stability of a foam which apparatus comprises (a) a light source, (b) a foam sample cell, (c) a light sensitive cell having a linear output voltage- or current-exposed area relationship, (d) a voltmeter or ammeter connected to the light sensitive cell and (e) means responsive to the output from the meter for integrating voltage or current time-curves directly and dividing this area by the difference in voltage or current between that observed in the absence of foam and that observed immediately after the foam has been formed to give the average foam lifetime; (a), (b) and (c) being in line and being enclosed in (f) a light-tight box.

The light source is suitably a fluorescent lamp.

The light sensitive cell may comprise a plurality of solar cells connected in series or a selenium photovoltaic cell with a low parallel resistance.

The means responsive to the output of the meter may be a microcomputer programmed to determine the average foam lifetime by integrating the voltage-time or current-time curves and dividing the area obtained from integration by the difference in voltage or current between that observed in the absence of foam and that observed immediately after the foam has been formed.

For live foam samples, the sample introduction system may comprise a sample pressurising vessel connected to a sample injection chamber leading to the sample cell.

For stabilised foam samples, the sample introduction system may simply be a valve-controlled line for the entry of liquid. In this case the sample cell must also contain means for the passage of gas through it.

The preferred means is a sintered base. The pore size of the sinter is important since sinters which are too fine become clogged easily whilst sinters which are too coarse allow liquid to drain through and form foams which are not sufficiently stable. For dealing with crude oil foams, the preferred maximum pore diameter is in the range 40 to 50 microns.

Either or preferably both sample introduction systems may be present.

Although intended primarily for determining the stability of crude oil foams, the apparatus is capable of determining the stability of foams derived from other sources such as detergents, chemical processes and sewage treatment.

The invention is illustrated with reference to FIGS. 1, 2 and 3 of the accompanying drawings, wherein FIG. 1 is an elevation and FIG. 2 a plan view of equipment for determining the stability of a stabilised foam, and FIG. 3 is a typical voltage/time curve.

With reference to FIGS. 1 and 2, the apparatus comprises a fluorescent lamp 1, a sample tube 2, and a strip of two solar cells 3, positioned in line and surrounded by a light-tight box 4.

A frosted glass plate 5 is positioned between the lamp 1 and the tube 2 and a clear glass plate 6 between the tube 2 and the cell 3.

The tube 2 is mounted on a foam rubber support 7. In order to generate foam from a liquid in the tube, gas is supplied to the base of the tube through sinters 8 of Grade No 2 (maximum pore diameter 40–50 $\mu$m).

The output from the solar cells 3 is connected to a digital volt meter 9 and from sockets 10 in parallel with the volt meter to a Hewlett-Packard 75C computer 11 which stores and analyses the data, and a chart recorder 12.

EXAMPLE 1

A charge of stabilised crude oil was placed in the sample tube and a foam was generated by sparging natural gas through the sinters into the crude oil. The lamp was then switched on and the gas supply stopped. As the foam thinned and collapsed, the amount of light reaching the solar cell strip increased and hence the voltage generated also increased. This was processed by the micro-computer and recorded on the chart recorder.

FIG. 3 is a typical chart. 13 represents the instant at which data collection commences, 14 that at which foam decay commences and 15 that by which foam decay is complete.

EXAMPLE 2

The apparatus was also used to study beer foam stability. It was not possible to use the apparatus in the previous manner, with foam generation by gas sparging, because the beer foams formed took much longer to collapse than crude oil foams. Over such long periods, the beer drained through the sinter. Therefore, beer foams were created in the following way. 5 cc samples of flat beer were pipetted into a test tube which was then stoppered and placed in the apparatus in the position usually taken by the gas sparging tube. This provided a base line voltage corresponding to complete foam collapse. The test tube was then removed from the apparatus, shaken and immediately replaced. Data collection commenced immediately. In each case foam decay was observed for about one hour. Foam collapse was never complete, even after several hours.

Average foam lifetmes were derived from experimental voltage-time curves using the following expression:

$$\frac{1}{V_{3600} - V_o} \int_0^{3600} (V_{3600} - V_t) dt$$

where
$V_{3600}$ = voltage after 3600 seconds of foam collapse
$V_0$ = initial voltage
$V_t$ = voltage after time t.

Average foam lifetimes measured in seconds are shown in the following Table.

Table

| Beer      | 1   | 2   | 3   | Average |
|-----------|-----|-----|-----|---------|
| Stout (A) | 908 | 740 | —   | 844     |
| Stout (B) | 744 | 759 | 730 | 744     |
| Brown Ale | 614 | 607 | 771 | 664     |
| Light Ale | 589 | 683 | 442 | 571     |

The reproducibility of the data is fair since the experiments were performed over a period of one week. It is likely that the compositions of the beers changed over this period.

We claim:

1. Apparatus for determining the stability of a foam comprising (a) a light source, (b) a foam sample cell, (c) a light sensitive cell having a linear output voltage-exposed area or current-exposed area relationship, (d) a voltmeter or ammeter connected to the light sensitive cell and (e) means responsive to the output from the voltmeter or ammeter for integrating a voltage-time current or a current time curve directly to obtain an area and dividing the obtained area by the difference in voltage or current between that observed in the absence of foam and that observed immediately after the foam has been formed to give the average foam lifetime; said light source, said foam sample cell and said light sensitive cell being positioned in line and being enclosed in a light-tight box.

2. Apparatus according to claim 1 wherein the light source is a fluorescent lamp.

3. Apparatus according to claim 1 wherein the light sensitive cell is a plurality of solar cells connected in series.

4. Apparatus according to claim 1 wherein the light sensitive cell is a selenium photovoltaic cell with a low parallel resistance.

5. Apparatus according to claim 1 wherein the means responsive to the output of the voltmeter ammeter is a microcomputer.

6. Apparatus according to claim 1 wherein the sample cell contains means for the passage of gas through it.

7. Apparatus according to claim 6 wherein the means is a sintered base.

8. Apparatus according to claim 7 wherein the maximum diameter of pores in the sintered base is in the range 40 to 50 microns.

* * * * *